(12) United States Patent
Graumann

(10) Patent No.: US 8,837,673 B2
(45) Date of Patent: Sep. 16, 2014

(54) METHOD FOR CORRECTLY GEOMETRICALLY ASSIGNING X-RAY IMAGES

(75) Inventor: Rainer Graumann, Hoechstadt (DE)

(73) Assignee: Siemens Aktiengesellschaft, Munich (DE)

( * ) Notice: Subject to any disclaimer, the term of this patent is extended or adjusted under 35 U.S.C. 154(b) by 309 days.

(21) Appl. No.: 13/419,665

(22) Filed: Mar. 14, 2012

(65) Prior Publication Data

US 2012/0236993 A1 Sep. 20, 2012

(30) Foreign Application Priority Data

Mar. 16, 2011 (DE) .......................... 10 2011 005 659

(51) Int. Cl.
*G01N 23/04* (2006.01)
*A61B 6/00* (2006.01)

(52) U.S. Cl.
CPC .............. *A61B 6/5235* (2013.01); *A61B 6/505* (2013.01); *A61B 6/4441* (2013.01); *A61B 6/547* (2013.01)
USPC ............................................ 378/63; 378/207

(58) Field of Classification Search
USPC ............................ 378/62, 162, 163, 164, 207
See application file for complete search history.

(56) References Cited

U.S. PATENT DOCUMENTS

| | | | |
|---|---|---|---|
| 5,347,570 A | 9/1994 | Haaks | |
| 6,227,704 B1 | 5/2001 | Bani-Hashemi et al. | |
| 6,229,873 B1 | 5/2001 | Bani-Hashemi et al. | |
| 6,379,041 B1 * | 4/2002 | Schuetz et al. | 378/205 |
| 6,447,163 B1 | 9/2002 | Bani-Hashemi et al. | |
| 6,473,489 B2 | 10/2002 | Bani-Hashemi et al. | |
| 2002/0118792 A1 * | 8/2002 | Graumann et al. | 378/163 |
| 2008/0285724 A1 * | 11/2008 | Dehler | 378/205 |
| 2009/0028296 A1 * | 1/2009 | Graumann et al. | 378/116 |

FOREIGN PATENT DOCUMENTS

| | | |
|---|---|---|
| DE | 10049103 A1 | 7/2001 |
| DE | 10108633 A1 | 9/2002 |
| DE | 102007034210 A1 | 2/2009 |
| EP | 0576066 A2 | 12/1993 |

OTHER PUBLICATIONS

Messmer, Peter, et al., "Image Fusion for Intraoperative Control of Axis in Long Bone Fracture Treatment," European Journal of Trauma, Dec. 13, 2006, pp. 555-561.

* cited by examiner

*Primary Examiner* — Glen Kao
(74) *Attorney, Agent, or Firm* — Laurence A. Greenberg; Werner H. Stemer; Ralph E. Locher

(57) ABSTRACT

In a method for correctly geometrically assigning x-ray images of a patient an optically operating recording device is attached to an x-ray device generating the x-ray images. A dimensionally stable marker surface which can be optically detected by the recording device and defines a reference system is fixed to the patient in a fixed relative position. The x-ray device is brought into a first and second recording position such that the recording device is directed toward the marker surface. In a recording position the x-ray device produces a first and second x-ray image of the patient and the recording device produces a first and second recording of the marker surface. The respective geometric position of the first and second x-ray image is determined in the reference system from the recordings. The first and second x-ray images are correctly geometrically assigned to one another in accordance with their position.

14 Claims, 3 Drawing Sheets

METHOD FOR CORRECTLY GEOMETRICALLY ASSIGNING X-RAY IMAGES

CROSS-REFERENCE TO RELATED APPLICATION

This application claims the priority, under 35 U.S.C. §119, of German application DE 10 2011 005 659.9, filed Mar. 16, 2011; the prior application is herewith incorporated by reference in its entirety.

BACKGROUND OF THE INVENTION

Field of the Invention

The invention relates to a method for correctly geometrically assigning x-ray images of a patient.

During the operative treatment of fractures of long hollow bones, care must be taken to ensure that the corresponding extremity axes of the patient are reproduced in their original form. For instance, with a femur fracture, the leg axis (avoiding varus or valgus position), the leg rotation and the leg length must be set correctly.

It is known to visually monitor the leg axis intra-operatively by an auxiliary device. To this end, the cable of an electrocautery is often used. It is also known to measure the leg length in comparison with the healthy leg of the patient and to visually align the leg rotation with the healthy leg.

An imaging device, e.g. an x-ray C-arm is also often intra-operatively available. X-ray devices of this type mostly contain a comparably small field of view of for instance only 15 cm diameter. A long hollow bone is considerably longer so that several x-ray images have to be recorded in order to image the whole bone. More recent methods enable the correct geometrical composition of individual x-ray recordings to form an overall image, from which the leg axis and the leg length can then be derived.

"Correct geometrical" means that with respect to the imaged patients, the images which are not related per se with respect to an imaginary overall image are in a correct position, in other words, are assigned to one another like image sections which are in a fixed position relative to one another. The real ratios on the patient are therefore imaged in a correct position on account of their opposite position and orientation.

Two approaches exist in order to compose the images: with the first approach, a very large number of x-ray images are recorded in pairs in each instance with a large image overlap in order therefrom to generate a coherent image. With a second approach, x-ray images are recorded with no overlap, e.g. an x-ray image of the hip, one of the knee and one of the ankle is recorded. On account of the absent overlap, a uniform reference system must nevertheless be created here for all (partial) images in order to correctly geometrically arrange and/or relate the individual images. The respective position determination of the imaging system would be conceivable here for instance on the basis of a conventional tracking system.

Alternatively, the article "'Image Fusion for Intra-operative Control of Axis in Long Bone Fracture Treatment', Peter Messmer et al., European Journal of Trauma 2006, No. 6, P. 555-561, Urban & Vogel" discloses a rigid marker plate with x-ray visible markers (location codes). The marker plate is placed under the patient so that parts of the same are visible in all partial images. The marker plate enables a correct geometrical assignment of the individual images to one another since corresponding x-ray visible location codes of the marker plate are visible in the x-ray image.

With the use of a marker or code plate of this type, the relevant x-ray markers are however always visible in the x-ray images in an interfering manner. The marker plate must also be positioned prior to supporting the patient, a subsequent positioning is no longer possible since this must be placed under the patient. The marker plate must be stored and also cleaned in the operating room. In some circumstances, the marker plate pushes through the patient rest in an interfering manner.

SUMMARY OF THE INVENTION

It is accordingly an object of the invention to provide a method for correctly geometrically assigning x-ray images which overcome the above-mentioned disadvantages of the prior art methods general type, which specifies an improved method for correctly geometrically assigning x-ray images of a patient.

With the foregoing and other objects in view there is provided, in accordance with the invention a method for correctly geometrically assigning x-ray images of a patient. The method includes: fixedly attaching an optically operating recording device to an x-ray device generating the x-ray images; fixing a dimensionally stable marker surface which can be optically detected by the recording device and defines a reference system to the patient in a fixed relative position; and bringing the x-ray device into a first and second recording position such that the recording device is directed toward the marker surface in each instance. In a respective recording position the x-ray device produces a first and second x-ray image of the patient and the recording device produces a first and second recording of the marker surface. A respective geometric position of the first and second x-ray image is determined in the reference system from the first and second recording. The first and second x-ray images are correctly geometrically assigned to one another in accordance with the respective geometric position.

An optically operating recording device is fixedly attached to an x-ray device which is used to generate x-ray images of the patient. "Fixedly" means that the recording device changes its recording direction and position if the x-ray device changes its corresponding alignment. Furthermore, a marker surface is fixed in a fixed relative position with respect to the patient, i.e. this reclines with respect to the patient. The marker surface defines a reference system, is dimensionally stable and can be optically detected by the recording device. The x-ray device is then moved into a first and second recording position such that the recording device is in each instance also directed toward the marker surface. In the respective recording position, the x-ray device produces a first and a second x-ray image of the patient, and the recording device in each instance simultaneously produces a first and second recording of the marker surface.

Since the recording device is fixedly fastened to the x-ray device but the marker surface is fixed to the patient in a fixed position, the optical field of view of the recording device moves toward the marker surface if the x-ray device also moves between the two x-ray images relative to the patient. On account of the known geometries of the overall arrangement, the respective geometric position of the first and second x-ray image can therefore be determined in the reference system from the first and second recording. At least the determination of the relative position of the first and second x-ray image is possible. Subsequently, the first and second x-ray images are correctly geometrically assigned to one another in accordance with their respective position in the reference system.

The recording device herewith operates optically, in other words not on an x-ray basis and requires a free optical line of sight to the marker surface in both recording positions respectively. A camera operating with visible or infrared light, a laser scanner or suchlike is conceivable for instance.

The marker surface is created such that a respective recording (of part) of the marker surface, e.g. an optical camera image, allows for a determination of the position of the recording device relative to the marker surface. In other words, in accordance with the invention an x-ray image and an associated recording of the marker surface are related to one another in each recording position. The geometric relationship of the x-ray images to one another can be directly determined from the geometric relationship of the recordings and/or optical images or video recordings known via the marker surface.

With oblique operating tables for instance, a recording situation results in which the marker surface is imaged into the recordings from a direction which is oblique hereto. The recording angle can then be determined from the distortion image of the marker surface. A square image section in itself then appears in the corresponding recording and/or image as a distorted trapeze or rhombus.

The inventive method is advantageous in that the marker surface is no longer visible in an interfering manner in the x-ray image as opposed to the afore-cited x-ray markers. Compared with the overlapping recording of x-ray images for calculating image mosaics, a significant saving of x-ray dose is made. The marker surface no longer has to be positioned in the beam path of the x-ray device and thus also not below the patient, in general the marker surface must definitely not be placed on the patient or on a table serving to support the patient. By applying the method to x-ray images which are created in each instance in pairs, any number of x-ray recordings can be correctly geometrically assigned to one another and/or related to one another.

In a preferred embodiment of the method, a first and second x-ray image are recorded such that the x-ray beams pass through the marker surface, whereby the marker surface is transparent to x-rays. The marker surface is herewith completely transparent to x-rays, i.e. does not provide any image contribution in the x-ray image.

In a preferred variant of this embodiment, the recording device, essentially only detects the section of the marker surface in the respective recording which is penetrated by the x-ray beams generating the corresponding x-ray image. In other words, a respective optical detection of the through-passage region of the x-ray beams for the respective x-ray image takes place in the vicinity of the patient.

In an alternative embodiment of the method, the marker surface is fixed to the patient as a rigid plate. For instance, the plate is placed on the part of the body of the patient to be x-rayed, e.g. his/her thigh, the patient herewith rests on an operating table for instance.

In a further advantageous embodiment of the method, the patient is placed on a top side of a patient couch and the marker surface is attached to the underside of the patient couch which is opposite the patient. In other words, the recording device is then in an undertable position during the respective recording of the x-ray images. The attachment to the underside can be combined particularly favorably with the penetration of the marker surface by x-ray beams during the image recording.

Alternatively, it would however also be conceivable to attach the marker surface to another point on the patient couch, i.e. its edge or its supporting foot.

In a variant of this embodiment, the marker surface is attached in a planar fashion to the underside. For instance, the marker surface then covers the whole table area in which patient regions to be imaged can be supported, in the line of sight at right angles to the table.

In a further variant of this embodiment, the marker surface is therefore attached so that it covers a whole area which comes into consideration for the passage of x-ray radiation in order to produce x-ray recordings.

In a preferred embodiment, an optical camera is used as a recording device.

In a further preferred embodiment, an x-ray C-arm system is used as an x-ray system. In particular, mobile C-arms come into consideration here.

In a preferred embodiment of the method, the x-ray images are recorded with at least approximately no overlap. This saves on x-ray dose for the patient compared with the afore-cited image mosaic recorded with significant overlap.

In a preferred embodiment of the method, the recording device is attached in the region of the x-ray source of the x-ray device. The recording device is therefore attached on the tube side and in a known relative position to the likewise known recording geometry of the x-ray device. Alternatively, the attachment in the detection region is also conceivable for instance.

In a preferred embodiment of the method, the optical beam path of the recording device is selected identical to the beam path of the x-ray radiation in order to produce x-ray images. In other words, the optical camera as a recording device then precisely images the geometry of the x-ray recording precisely. The optical images in the form of recordings correspond exactly to the roentgenological angle of view of the x-ray beams from the recording positions of the x-ray images. In particular, an optical mirror which is integrated into the beam path of the x-ray beams is suitable here, comparable with the CAMC principle known from published, non-prosecuted German patent application DE 100 49 103 A1, corresponding to U.S. Pat. Nos. 6,473,489, 6,447,163, 6,229,873, and 6,227,704.

In a preferred embodiment the marker surface is a sequence of different, optically detectable pairs of figures in each instance, the respective spatial position of which is known relative to the marker surface. In other words, each figure represents a clearly identifiable location identifier, which allows the afore-cited geometric assignment. An image of part of the marker surface is therefore clearly identifiable with regard to its position within the marker surface.

In a preferred embodiment of this variant, each marking contains a bar code, which specifies the respective spatial position of the marking in the marker surface. The bar code is for instance a 2 D and/or n×n barcode, the spatial and/or relative position a 2 D position with a flat marker surface, otherwise for instance a spatial position with a spatially curved or extended marker surface.

In a preferred embodiment of the method, the marker surface is permanently attached, in particular as described above, to the patient couch. The required relative local fixing between the marker surface and the patient position herewith results in particular for a patient reclining on the patient couch. The marker surface therefore forms a rigid plate or an imprint on a wall or another reclining object in the treatment room for instance.

Other features which are considered as characteristic for the invention are set forth in the appended claims.

Although the invention is illustrated and described herein as embodied in a method for correctly geometrically assigning x-ray images, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
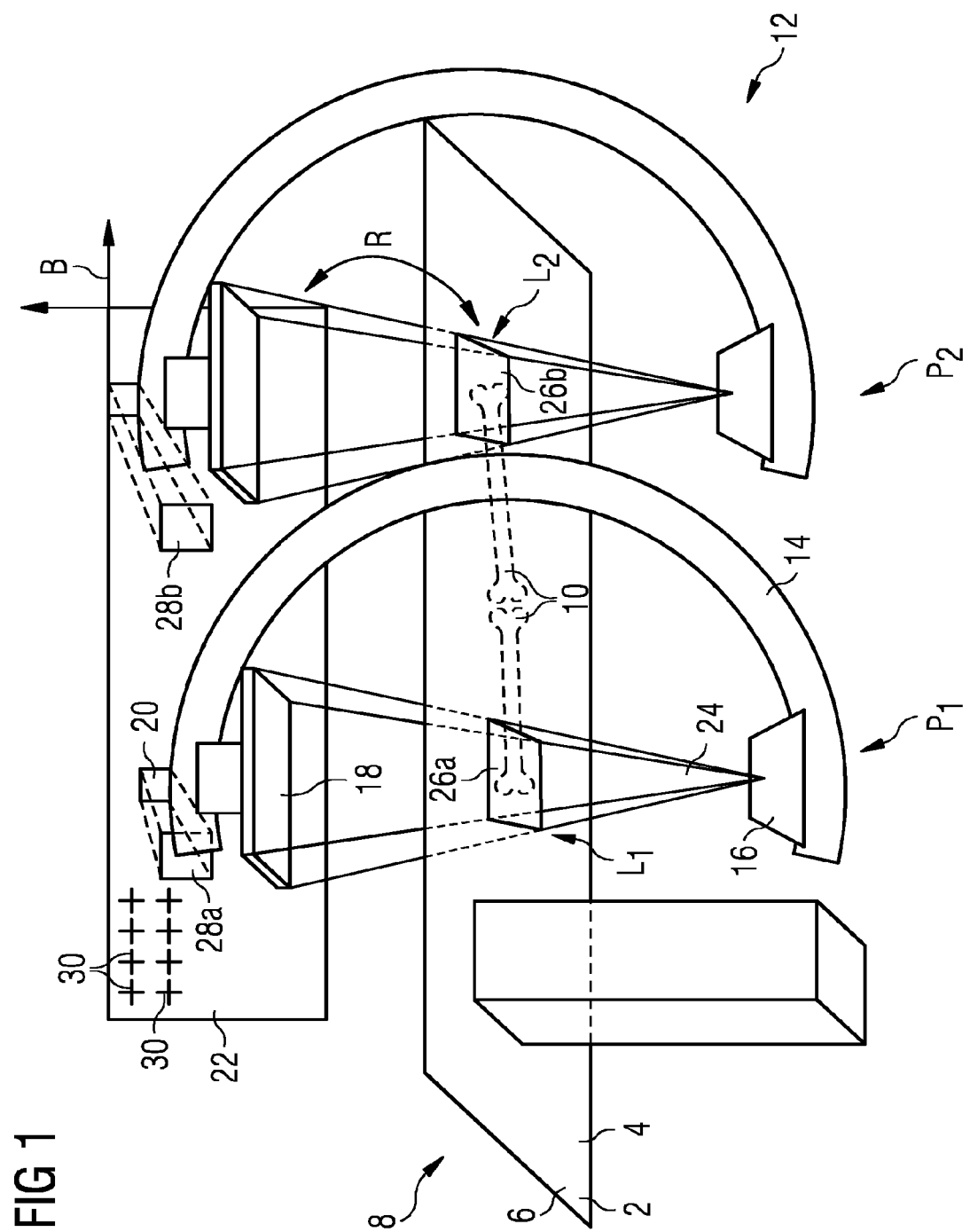
FIG. 1 is a diagrammatic, perspective oblique view of an x-ray system with a wall-fixed marker surface.

Referring now to the figures of the drawing in detail and first, particularly, to FIG. 1 thereof, there is shown a perspective oblique view of a patient couch 2 and/or its underside 4. A patient 8 is supported on a opposite top side 6 of the patient couch 2, of which only two long hollow bones 10 of his/her leg are shown. Following a bone fracture, the leg and/or the bones 10 of the patient 8 is/are to be set. This is to take place operatively using x-ray control.

An x-ray device 12 in the form of an x-ray C-arm 14 containing an x-ray source 16 and x-ray detector 18 are therefore also shown in FIG. 1. In accordance with the invention, a recording device 20 in the form of an optical camera is attached to the x-ray device 12 and/or x-ray C-arm 14. A marker surface 22 which defines a reference system B is also fixed in a fixed relative position R to the patient 8. By way of example this is fixedly attached to a wall of an operating room.

The x-ray device 12 is initially brought into a first recording position P1. By emitting x-ray beams 24, a first x-ray image 26a of the patient 8 and/or the bones 10, here the hip joint, is produced. In the same recording position P1, a first recording 28a of the marker surface 22 is produced by the recording device 20. The first recording 28a forms a first section of the marker surface 22.

The x-ray device 12 is then brought into a second recording position P2 and a second x-ray image 26b of the bones 10, here the ankle joint, is in turn produced there In the same recording position P2, a second recording 28b is also produced which shows a second section of the marker surface 22.

The x-ray images 26a, b are only shown symbolically in the region of the patient couch 2 as an image of the patient 8 resting thereupon.

In the example the x-ray images 26a, b each form the hip and ankle joint of the leg of the patient 8 in order to set the entire leg correctly with respect to leg axis, leg rotation and leg length with the aid of the two x-ray images 26a, b. Since the two x-ray images 26a, b are recorded without any overlap, in other words they do not comprise a shared image content, these must be correctly geometrically assigned to one another. This takes place as now described.

In each of the positions P1, 2, the recording device 20 has recorded a specific section of the marker surface 22 in the form of recordings 28a, b. Due to the fixed arrangement of the recording device 20 on the x-ray device 12, the respective recording 28a, b is strictly correlated with the respective spatial position and roentgenological line of sight and/or recording position P1, 2 of the x-ray device 12 in the reference system B. In other words, the precise recording geometries of the x-ray images 26a, b in the reference system B are therefore known in positions P1, 2. Since on the other hand the recording geometry of the x-ray device 12 is itself known, a geometric respective position L1, 2 of the respective x-ray images 26a, b in the reference system B is determined on the basis of the recordings 28a, b.

Depending on the definition of the reference system B, the absolute positions L1, 2, nevertheless at least the relative difference of the positions L1, 2 are possibly known from the relative difference of the recordings 28a, b of the marker surface 22. The recordings 28a, b and thus the x-ray images 26a, b are already correctly geometrically assigned relative to one another on the basis hereof.

In order to be able to identify the respective position of the sections of the marker surface 22 imaged in the recordings 28a, b, this comprises a sequence of in each instance pairs of different optically detectable markings. The respective spatial position P of each marking 30 on the marker surface 22 is known. The markings 30 are also distinguishable in pairs. The markings 30 are only shown symbolically in FIG. 1.

Figure 2:
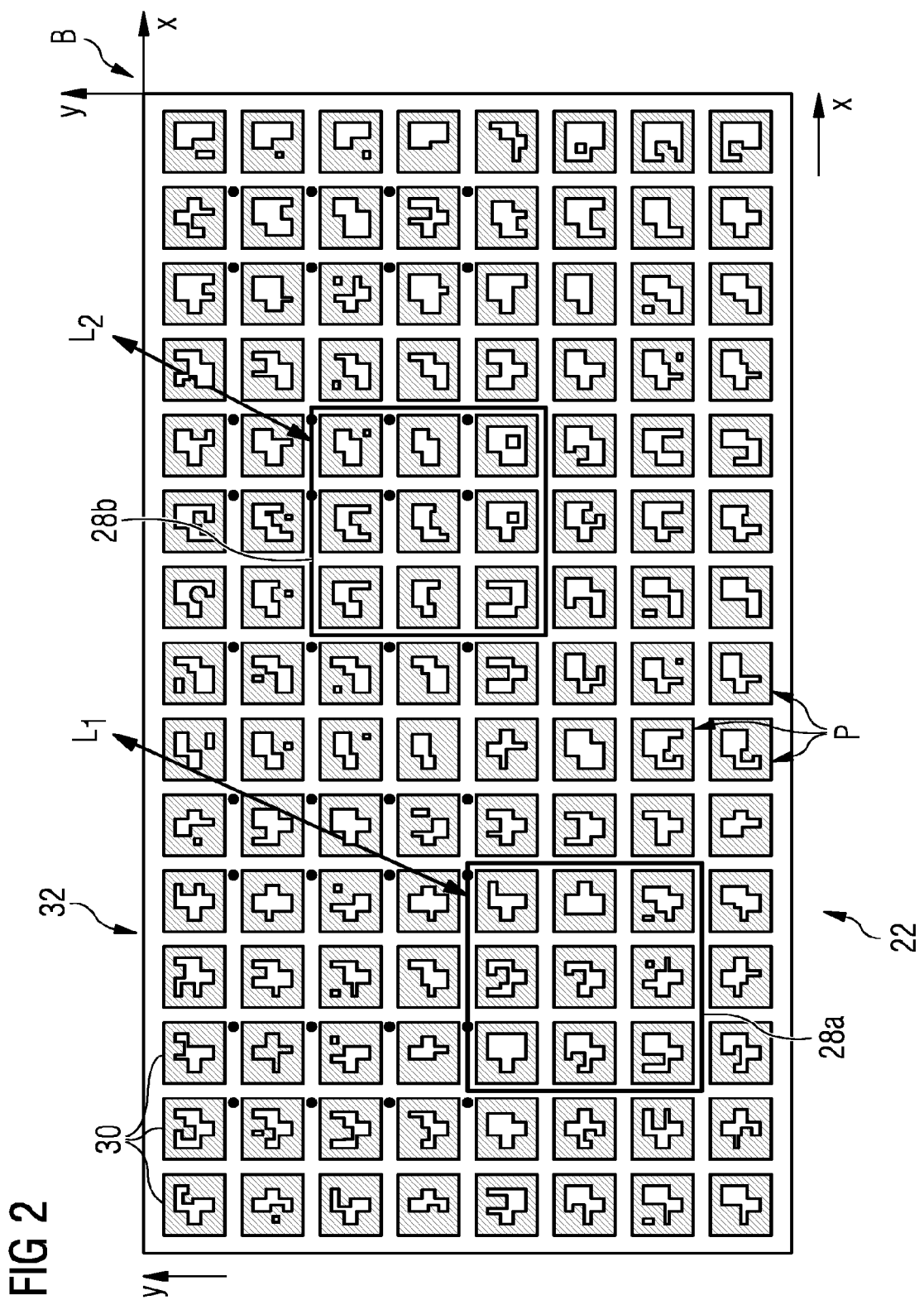
FIG. 2 is a detailed illustration of the marker surface from FIG. 1.

FIG. 2 shows in detail the marker surface 22 and the markings 30 from FIG. 1. Each marking 30 represents a two-dimensional barcode 32, which clearly reproduces the respective spatial position P of the respective marking 30 with respect to x and y coordinates on the marker surface 22 and thus in the reference system B. The corresponding position of two recordings 28a, b of the marker surface 22 relative to one another can therefore be determined from the respective x and y coordinates in marking 30 and/or from the barcode 32. The positions L1, 2 of the corresponding x-ray images 26a, b and/or at least their relative position to one another can finally be determined herefrom as described above.

Figure 3:
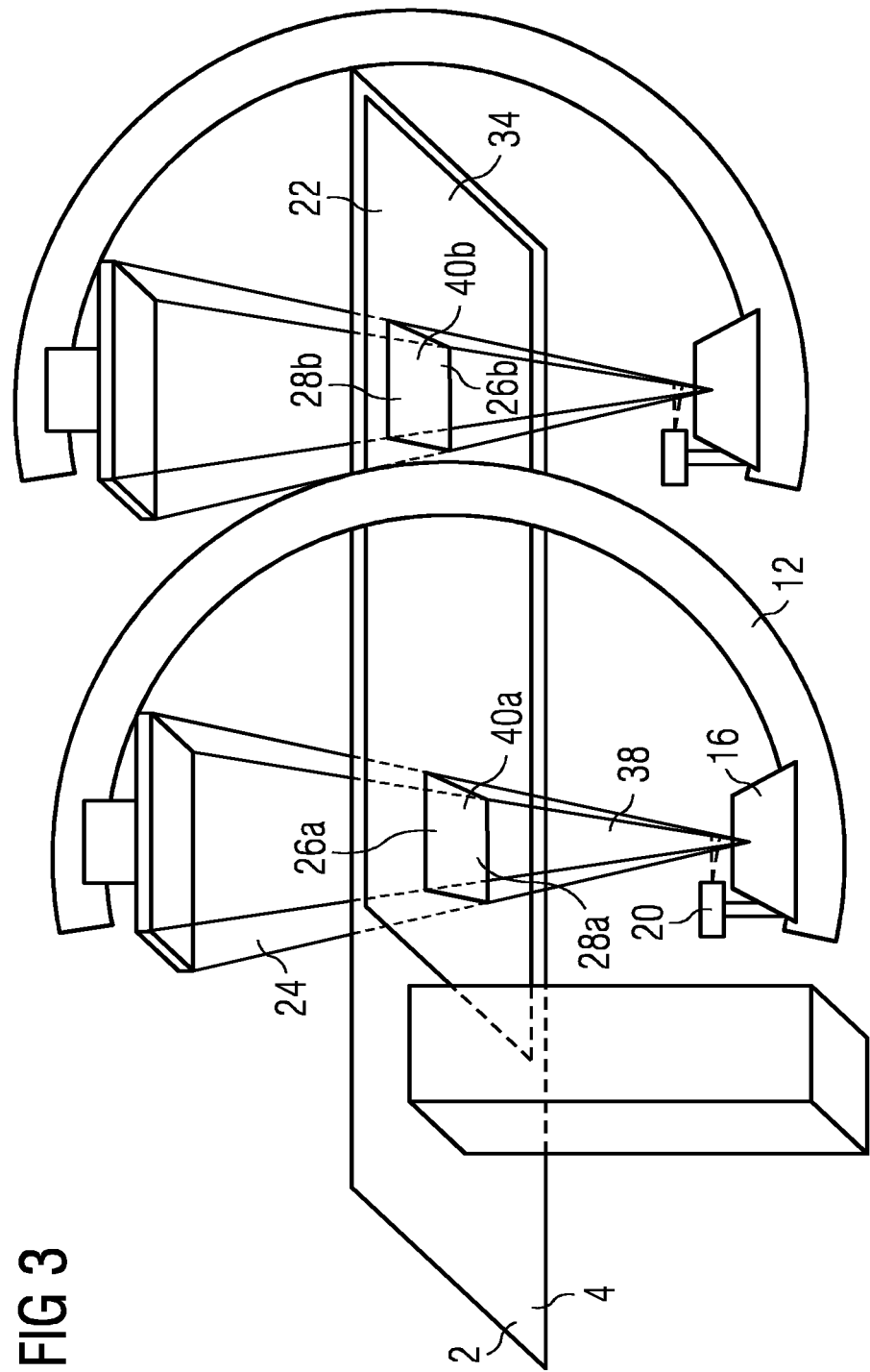
FIG. 3 is a diagrammatic, perspective oblique view of an alternative x-ray system with the marker surface on the patient couch.

FIG. 3 shows an alternative embodiment of the invention. The marker surface 22 is directly attached here to the underside 4 of the patient couch 2. This attachment takes place such that this covers the entire area 34 of the patient couch 2, which comes into consideration for the recording of x-ray images, in other words the penetration with x-rays 24. Furthermore, in the embodiment according to FIG. 3, the recording device 20 in the form of the video camera is also attached to the x-ray device 12 in the region of the x-ray source 16. The recording device 20 operates according to the so-called CAMC principle: an optical mirror 36 which is transparent to x-rays is therefore introduced into the beam path of the x-ray rays 24 such that the optical beam path 38 of the recording device 20 corresponds to that of the x-ray beams 24 in the region downstream of the mirror 36. The recordings 28a, b in each instance therefore form at least approximately the region of the marker surface 22, which corresponds to the through-passage surface 40a, b for x-ray beams 24 for the respective x-ray images 28a, b. In this embodiment, the marker surface 22 together with the markings 30 is completely transparent to x-rays, so that this does not contribute in any way to the respective x-ray image 26a, b. In FIG. 3, the marker surface 22 is permanently attached to the underside 4, e.g. imprinted hereon.

The invention claimed is:

1. A method for correctly geometrically assigning x-ray images of a patient, which comprises the steps of:
   fixedly attaching an optically operating recording device to an x-ray device generating the x-ray images;
   seating the patient on a top side of a patient couch;

fixing a dimensionally stable marker surface directly onto an underside of the patient couch and which can be optically detected by the recording device and defines a reference system to the patient in a fixed relative position;

bringing the x-ray device into a first and second recording position such that the recording device is directed toward the marker surface in each instance, in a respective recording position the x-ray device producing a first and second x-ray image of the patient and the recording device producing a first and second recording of the marker surface;

determining a respective geometric position of the first and second x-ray image in the reference system from the first and second recording; and correcting geometrically the first and second x-ray image assigned to one another in accordance with the respective geometric position.

2. The method according to claim 1, which further comprises recording the first and second x-ray image such that x-ray beams producing the first and second x-ray images pass through the marker surface, whereby the marker surface is transparent to x-rays.

3. The method according to claim 2, wherein the recording device records a subarea of the marker surface which is penetrated by the x-ray beams as the first and second recordings.

4. The method according to claim 1, which further comprises fixing the marker surface to the patient as a rigid plate.

5. The method according to claim 1, which further comprises attaching the marker surface in a planar fashion to the underside of the patient couch.

6. The method according to claim 5, which further comprises attaching the marker surface such that the marker surface covers a whole area, which comes into consideration for the passage of x-rays in order to produce the first and second x-ray images.

7. The method according to claim 1, which further comprises using an optical camera as the recording device.

8. The method according to claim 1, which further comprises using an x-ray C-arm system as the x-ray device.

9. The method according to claim 1, which further comprises recording the x-ray images at least approximately without overlap.

10. The method according to claim 1, which further comprises attaching the recording device in a region of an x-ray source of the x-ray device.

11. The method according to claim 1, which further comprises selecting an optical beam path of the recording device to be identical to a beam path of x-ray beams in order to produce the x-ray images.

12. The method according to claim 1, wherein the marker surface is a sequence of optically detectable markings which differ in pairs in each instance, a respective spatial position of which is known in the marker surface.

13. The method according to claim 12, wherein each of the optically detectable markings contains a barcode of its spatial position in the marker surface.

14. The method according to claim 1, which further comprises attaching the marker surface permanently.

* * * * *